United States Patent [19]

Buschmann et al.

[11] Patent Number: 4,673,683
[45] Date of Patent: Jun. 16, 1987

[54] FUNGICIDAL PIPERIDINE DERIVATIVES

[75] Inventors: Ernst Buschmann, Ludwigshafen; Ludwig Schuster, Limburgerhof; Norbert Goetz, Worms; Ernst-Heinrich Pommer, Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 772,714

[22] Filed: Sep. 5, 1985

[30] Foreign Application Priority Data

Sep. 8, 1984 [DE] Fed. Rep. of Germany ....... 3433036

[51] Int. Cl.$^4$ .................. A01N 43/40; C07D 211/22; C07D 211/46
[52] U.S. Cl. .................................. 514/317; 514/327; 514/331; 546/216; 546/222; 546/233; 546/234; 546/236; 546/238; 546/239; 546/240
[58] Field of Search ............... 546/240, 216, 222, 233, 546/234, 236, 238, 239; 514/317, 327, 331

[56] References Cited

FOREIGN PATENT DOCUMENTS 0000333 7/1982 European Pat. Off. ............ 546/240

OTHER PUBLICATIONS

*Chemical Abstracts*, 90:152004a (1979) [Mimmele et al., Ger. Offen. 2,727,482, 1/11/79].

Primary Examiner—Richard A. Schwartz
Attorney, Agent, or Firm—Keil & Weinkauf

[57] ABSTRACT

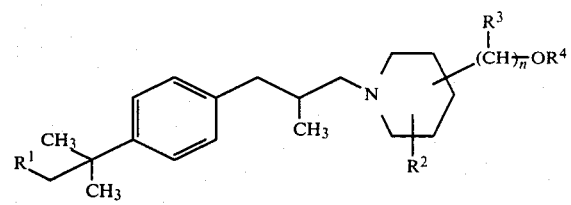

where
R$^1$ is hydrogen, alkyl or halogen,
R$^2$ and R$^3$ are hydrogen or alkyl,
R$^4$ is hydrogen, alkyl, alkenyl, alkynyl, haloalkyl, haloalkenyl, unsubstituted or substituted aralkyl, COR$^5$, CO$_2$R$^6$ or CONR$^7$R$^8$,
R$^5$ and R$^6$ are alkyl, unsubstituted or substituted aryl or unsubstituted or substituted aralkyl,
R$^7$ and R$^8$ are hydrogen, alkyl, unsubstituted or substituted aryl or unsubstituted or substituted aralkyl and
n is 0, 1, 2 or 3, and its plant-tolerated acid addition salts, excluding the compounds where, simultaneously, R$^4$ is hydrogen, acetyl or propionyl, n is 0 or 1 and R$^1$, R$^2$ and R$^3$ are hydrogen, and fungicides containing the novel piperidines and salts.

3 Claims, No Drawings

FUNGICIDAL PIPERIDINE DERIVATIVES

The present invention relates to novel piperidine derivatives, processes for their preparation, their use as fungicides, fungicidal mixtures containing the novel compounds as active ingredient, processes for the preparation of such fungicidal mixtures and methods of control of harmful fungi by means of these active ingredients.

The use of phenylpropylpiperidines, especially of N-[3-(4-tertiary-butylphenyl)-2-methyl-propyl]-4-hydroxypiperidine and the corresponding -3-hydroxymethylpiperidine compound, as fungicides is known (European Pat. No. 333). However, the effect of the known fungicides is unsatisfactory for some applications, especially when low amounts and low concentrations are used.

We have found that piperidines of the formula

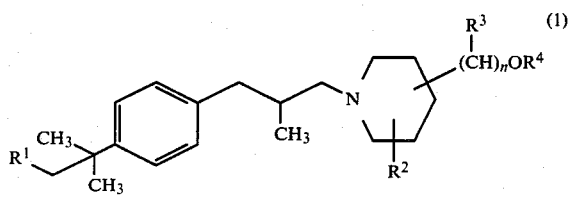

where
$R^1$ is hydrogen, alkyl or halogen,
$R^2$ and $R^3$ are hydrogen or alkyl,
$R^4$ is hydrogen, alkyl, alkenyl, alkynyl, haloalkyl, haloalkenyl, unsubstituted or substituted aralkyl, $COR^5$, $CO_2R^6$ or $CONR^7R^8$,
$R^5$ and $R^6$ are alkyl, unsubstituted or substituted aryl or unsubstituted or substituted aralkyl,
$R^7$ and $R^8$ are hydrogen, alkyl, unsubstituted or substituted aryl or unsubstituted or substituted aralkyl and
n is 0, 1, 2 or 3,
and their plant-tolerated acid addition salts, excluding the compounds where, simultaneously, $R^4$ is hydrogen, acetyl or propionyl, n is 0 or 1 and $R^1$, $R^2$ and $R^3$ are hydrogen, have a very good fungicidal action superior to that of the known piperidines.

$R^1$ is, for example, hydrogen, $C_1$-$C_6$-alkyl, eg. methyl, ethyl, propyl, n-butyl, isopropyl, isobutyl, n-pentyl or n-hexyl, chlorine, bromine or fluorine.

$R^2$ and $R^3$ are, independently of one another, for example, hydrogen or $C_1$-$C_6$-alkyl, eg. methyl, ethyl, propyl, isopropyl, n-butyl, isobutyl, n-pentyl or n-hexyl.

$R^4$ is, for example, hydrogen, $C_1$-$C_6$-alkyl, eg. methyl, ethyl, propyl, isopropyl, n-butyl, isobutyl, n-pentyl or n-hexyl, allyl, propargyl, trichloroallyl ($CH_2CCl=CCl_2$), benzyl, halobenzyl, eg. 4-chlorobenzyl, dihalobenzyl, eg. 2,4-dichlorobenzyl, $C_1$-$C_4$-alkylbenzyl, eg. 4-methylbenzyl or 4-tert.-butylbenzyl, trifluoromethylbenzyl, eg. 4-$CF_3$-benzyl, or alpha- or beta-naphthylmethyl.

$R^5$ and $R^6$ are, independently of one another, for example $C_1$-$C_4$-alkyl, eg. methyl, ethyl, n-propyl, iso-propyl or n-butyl, phenyl, halophenyl, eg. 4-chlorophenyl or 3-chlorophenyl, dihalophenyl, eg. 3,5-dichlorophenyl or 2,4-dichlorophenyl, $C_1$-$C_4$-alkylphenyl, eg. 4-methylphenyl, benzyl or halobenzyl, eg. 4-chlorobenzyl.

$R^7$ and $R^8$ are, independently of one another, for example, hydrogen, $C_1$-$C_4$-alkyl, eg. methyl, ethyl, n-propyl or iso-propyl, phenyl, halophenyl, eg. 4-chlorophenyl or 3-chlorophenyl, dihalophenyl, eg. 3,5-dichlorophenyl, benzyl or halobenzyl, eg. 4-chlorobenzyl.

Examples of acid addition salts are the salts with inorganic or organic acids, for example hydrochloric acid, hydrobromic acid, sulfuric acid, phosphoric acid, acetic acid, propionic acid and dodecylbenzenesulfonic acid.

The novel compounds may be used as fungicides.

Important starting compounds for the preparation of the piperidines are the phenylalkyl halides of the formula (2) and the corresponding aldehydes of the formula (3)

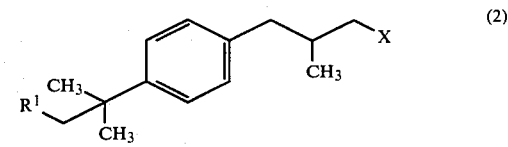

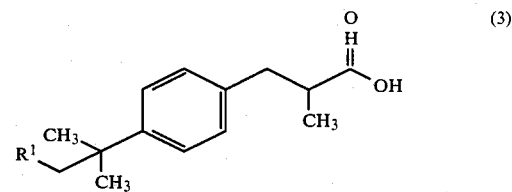

which are described in European Pat. No. 9077 and German Laid-Open Application DEOS No. 2,752,036. The synthesis of the novel compounds may, for example, be carried out as shown below, with the various radicals having the meanings given above and X being chlorine or bromine.

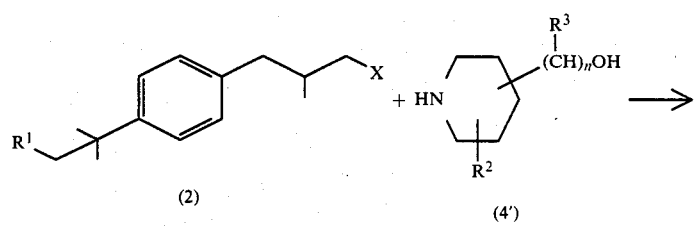

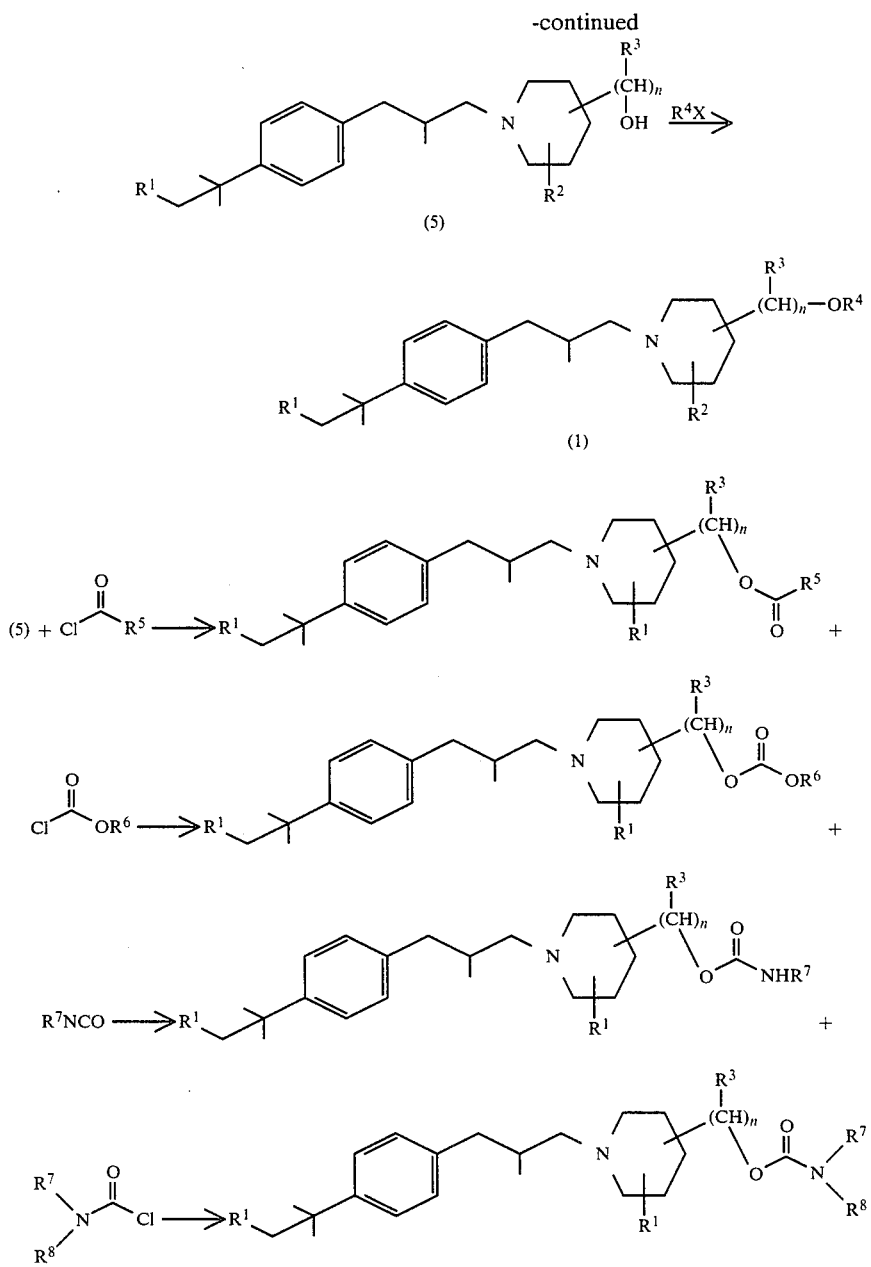

Examples of suitable amines of the formula 4'

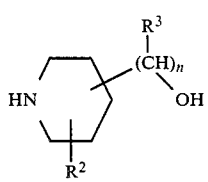

are 3-hydroxypiperidine, 4-hydroxypiperidine, 4-hydroxymethylpiperidine, 3-hydroxymethylpiperidine, 4-hydroxyethylpiperidine, 3-(1-hydroxyethyl)-piperidine, 3-(1-hydroxypropyl)-piperidine, 3-(1-hydroxybutyl)-piperidine, 3-(1-hydroxypentyl)-piperidine, 3-(1-hydroxyhexyl)-piperidine, 3-(1-hydroxy-isobutyl)-piperidine, 3-(1-hydroxyisopentyl)-piperidine, 3-(1-hydroxybutyl)-4-propyl-piperidine, 3-(1-hydroxypentyl)-4-butyl-piperidine, and 3-(1-hydroxyhexyl)-4-pentyl-piperidine.

The piperidines listed above may be obtained in a conventional manner by hydrogenating the corresponding hydroxypyridines or acylpyridines. The synthesis of acylpyridines is described in German Laid-Open Application DEOS No. 3,126,819.

The methods and examples which follow illustrate the preparation of the novel compounds and of their intermediates.

Method 1

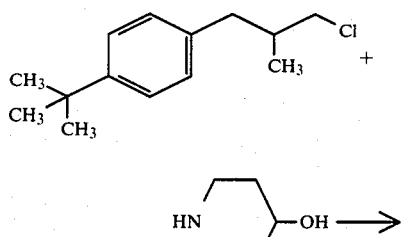

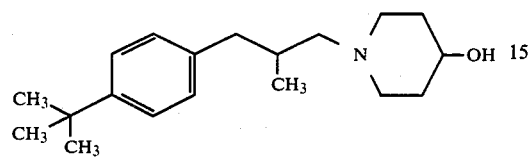

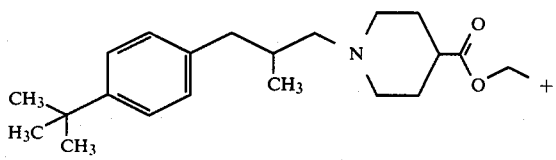

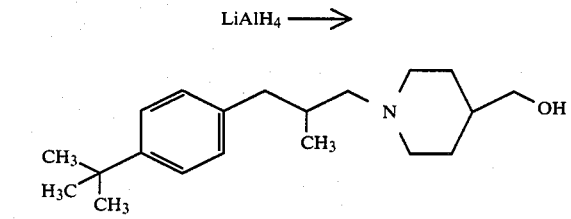

106 g of Na₂CO₃ are added to a solution of 112 g of 3-(4-tert.-butylphenyl)-2-methyl-propyl chloride and 50 g of 4-hydroxypiperidine in 1 liter of dimethylformamide (DMF). The batch is heated at 150° C. for 15 hours and then concentrated, and the residue is taken up in CH₂Cl₂. The CH₂CL₂ phase is washed with water, dried over Na₂SO₄ and concentrated. Distillation of the crude product gives 103 g of N-[3-(4-tert.-butylphenyl)-2-methyl-propyl]-4-hydroxypiperidine [A] as a pale yellowish oil. Boiling point 175°–178° C./0.4 mbar.

[A] is an intermediate for the preparation of compounds No. 49, 51, 52, 53, 54 and 55.

Method 2

A solution of 41.4 g of N-[3-(4-tert.-butylphenyl)-2-methyl-propyl]-4-carbethoxy-piperidine in 100 ml of absolute diethyl ether is added dropwise to a suspension of 10 g of LiALH₄ in 100 ml of absolute ether. An exothermic reaction ensues and the ether refluxes. When the reaction has subsided, the mixture is heated under reflux for 4 hours. 100 ml of water are then slowly added dropwise, with ice cooling. 500 ml of diethyl ether are added, the top layer is decanted and the smeary residue is triturated twice more with ether. The combined ether phases are washed with water, dried over Na₂SO₄ and concentrated. Distillation of the residue gives 21 g of N-[3-(4-tert.-butylphenyl)-2-methyl-propyl]-4-hydroxymethylpiperidine [B]. Boiling point 175°–178° C./0.2 mbar.

[B] is an intermediate in the preparation of compounds No. 56 and 57.

PREPARATION EXAMPLE 1

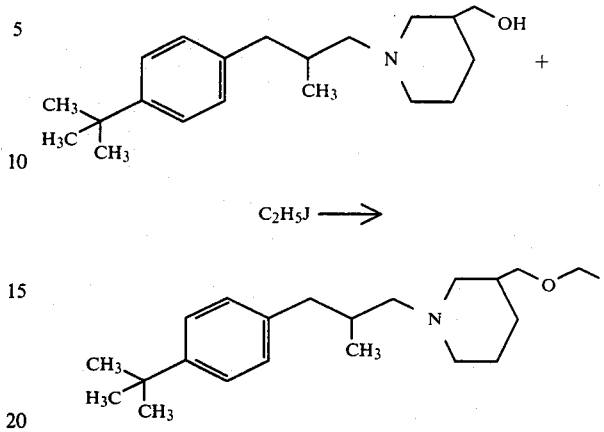

13.5 g of an 80% strength suspension of NaH in paraffin are added, a little at a time, to a solution of 60.6 g of N-[3-(4-tert.-butylphenyl-2-methyl-propyl]-3-hydroxymethylpiperidine in 110 ml of dimethyl sulfoxide (DMSO) and 390 ml of diethyl ether. The mixture is heated under reflux for 1 hour, 62.4 g of ethyl iodide are added dropwise and stirring is continued for 30 minutes. After cautious hydrolysis with 1.2 liters of H₂O, the water initially being added dropwise, slowly, the mixture is extracted with diethyl ether, washed with aqueous sodium thiosulfate solution and with water, dried over Na₂SO₄ and concentrated. Examination of the crude product by gas chromatography shows that there has been only 80% conversion. The crude product is therefore again reacted with the same amounts of NaH and C₂H₅I. Working-up is carried out as above. Distillation gives 58 g of a pale yellowish oil. Boiling point 160°–164° C./0.4 mbar (Compound No. 13).

PREPARATION EXAMPLE 2

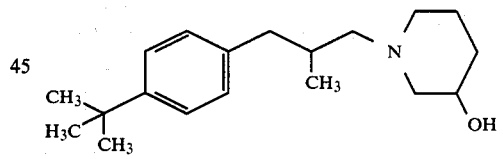

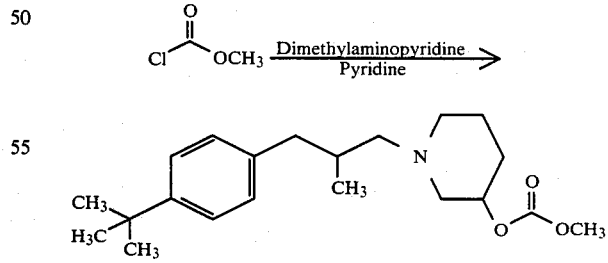

16 g of methyl chloroformate are added dropwise to a solution of 40 g of N-[3-(4-tert.-butylphenyl)-2-methyl-propyl]-3-hydroxypiperidine, 132 g of pyridine and 0.2 g of 4-dimethylaminopyridine in 500 ml of tetrahydrofuran (THF). The mixture is stirred for 15 hours at room temperature and then concentrated, the residue is taken up in CH₂Cl₂, this solution is washed with water, with dilute NaOH solution and again with water, dried over Na$_2$SO$_4$ and concentrated, and the residue is distilled. Yield, 16 g of N-[3-(4-tert.-butylphenyl)-2-methyl-propyl]-3-oxycarbomethoxy-piperidine. Boiling point 180°–182° C./0.3 mbar. (Compound No. 44).

The piperidines listed in the Tables which follow can be prepared in a corresponding manner.

TABLE 2

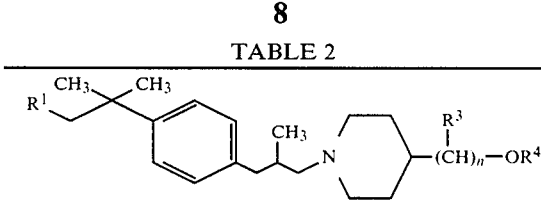

| Compound no. | R$^1$ | R$^3$ | R$^4$ | n | B.p./mbar |
|---|---|---|---|---|---|
| 49 | H | — | CH$_3$ | 0 | 152–156° C./0.4 |
| 50 | CH$_3$ | — | CH$_3$ | 0 | |
| 51 | H | — | C$_2$H$_5$ | 0 | 158–160° C./0.4 |
| 52 | Cl | — | C$_2$H$_5$ | 0 | |
| 53 | H | — | allyl | 0 | |
| 54 | H | — | benzyl | 0 | |
| 55 | H | — | CO$_2$CH$_3$ | 0 | |

TABLE 1

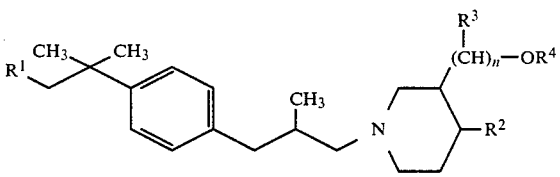

| Compound no. | R$^1$ | R$^2$ | R$^3$ | R$^4$ | n | B.p./mbar |
|---|---|---|---|---|---|---|
| 1 | H | H | — | CH$_3$ | 0 | 145–152° C./0.4 |
| 2 | CH$_3$ | H | — | CH$_3$ | 0 | 156–162° C./0.4 |
| 3 | Cl | H | — | CH$_3$ | 0 | |
| 4 | H | H | — | C$_2$H$_5$ | 0 | 145–153° C./0.4 |
| 5 | CH$_3$ | H | — | C$_2$H$_5$ | 0 | |
| 6 | Cl | H | — | C$_2$H$_5$ | 0 | |
| 7 | H | H | — | n-C$_3$H$_7$ | 0 | |
| 8 | H | H | — | allyl | 0 | 163–168° C./0.4 |
| 9 | CH$_3$ | H | — | allyl | 0 | |
| 10 | H | H | — | benzyl | 0 | 202–204° C./0.4 |
| 11 | CH$_3$ | H | — | benzyl | 0 | |
| 12 | H | H | — | 4-Cl—benzyl | 0 | |
| 13 | H | H | H | CH$_3$ | 1 | 160–164° C./0.4 |
| 14 | CH$_3$ | H | H | CH$_3$ | 1 | |
| 15 | H | H | H | C$_2$H$_5$ | 1 | 147–154° C./0.3 |
| 16 | H | H | H | n-propyl | 1 | |
| 17 | H | H | H | iso-propyl | 1 | |
| 18 | H | H | H | allyl | 1 | 170–182° C./0.5 |
| 19 | CH$_3$ | H | H | allyl | 1 | |
| 20 | H | H | H | benzyl | 1 | 226–230–230° C./0.9 |
| 21 | H | H | H | 2,4-Cl$_2$—benzyl | 1 | 224–225° C./0.3 |
| 22 | H | H | H | 4-CH$_3$—benzyl | 1 | |
| 23 | H | H | H | 3-CF$_3$—benzyl | 1 | |
| 24 | H | H | CH$_3$ | H | 1 | 180–186° C./0.9 |
| 25 | H | H | CH$_3$ | CH$_3$ | 1 | 153–162° C./0.4 |
| 26 | H | H | CH$_3$ | allyl | 1 | |
| 27 | H | H | CH$_3$ | benzyl | 1 | |
| 28 | CH$_3$ | H | CH$_3$ | H | 1 | |
| 29 | CH$_3$ | H | CH$_3$ | CH$_3$ | 1 | |
| 30 | CH$_3$ | H | CH$_3$ | C$_2$H$_5$ | 1 | |
| 31 | H | n-propyl | n-propyl | H | 1 | |
| 32 | H | n-propyl | n-propyl | CH$_3$ | 1 | |
| 33 | H | n-butyl | n-butyl | H | 1 | |
| 34 | H | n-butyl | n-butyl | CH$_3$ | 1 | |
| 35 | H | n-pentyl | n-pentyl | H | 1 | |
| 36 | H | n-pentyl | n-pentyl | CH$_3$ | 1 | |
| 37 | H | H | n-propyl | H | 1 | |
| 38 | H | H | n-propyl | CH$_3$ | 1 | |
| 39 | H | H | n-propyl | allyl | 1 | |
| 40 | H | H | n-butyl | H | 1 | |
| 41 | H | H | n-butyl | CH$_3$ | 1 | |
| 42 | H | H | n-pentyl | H | 1 | 180–182° C./0.3 |
| 43 | H | H | n-pentyl | CH$_3$ | 1 | |
| 44 | H | H | — | CO$_2$CH$_3$ | 0 | 180–182° C./0.3 |
| 45 | H | H | — | CONHCH$_3$ | 0 | |
| 46 | H | H | H | CO$_2$C$_2$H$_5$ | 1 | 180° C./0.3 |
| 47 | H | H | H | propargyl | 1 | 168–172° C./0.3 |
| 48 | H | H | H | CH$_2$CCl=CCl$_2$ | 1 | |
| 66 | H | H | CH$_3$ | COCH$_3$ | 1 | 165° C./0.3 |
| 67 | H | H | — | CO$_2$C$_2$H$_5$ | 0 | 182° C./0.3 |
| 68 | H | H | H | CO$_2$CH$_3$ | 1 | 184–187° C./0.3 |

TABLE 2-continued

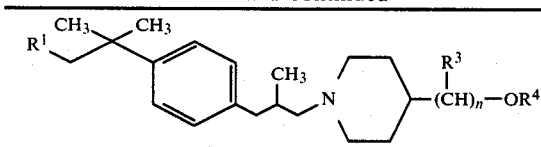

| Compound no. | R¹ | R³ | R⁴ | n | B.p./mbar |
|---|---|---|---|---|---|
| 56 | H | H | CH₃ | 1 | |
| 57 | H | H | C₂H₅ | 1 | |
| 58 | H | CH₃ | H | 1 | |
| 59 | H | CH₃ | CH₃ | 1 | |
| 60 | H | H | H | 2 | 186–190° C./0.4 |
| 61 | CH₃ | H | H | 2 | |
| 62 | H | H | CH₃ | 2 | 169–175° C./0.4 |
| 63 | H | H | allyl | 2 | 185–190° C./0.4 |
| 64 | H | H | acetyl | 2 | |
| 65 | H | H | CO₂CH₃ | 2 | |

The novel compounds have an excellent action on a broad spectrum of plant-pathogenic fungi, especially from the Ascomycetes and Basidiomycetes classes. Some of them have a systemic action and may be used as soil or foliar herbicides.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: *Erysiphe graminis* in cereals, *Erysiphe cichoriacearum* in Cucurbitaceae, *Podosphaera leucotricha* in apples, *Uncinula necator* in grapes, *Puccinia* species in cereals, *Rhizoctonia solani* in cotton, *Ustilago* species in cereals and sugarcane, *Venturia inaequalis* (scab) in apples, *Septoria nodorum* in wheat, *Botrytis cinerea* in strawberries and grapes, *Pyricularia oryzae* in rice, *Alternaria solani* in potatos and tomatoes, *Verticillum* species in cotton and vegetables, and *Plasmopara viticola* in grapes.

The novel compounds are used by spraying or dusting the plants with the active ingredients, or treating the seed of plants with the active ingredients. Application may be effected before or after infection of the plants or seed by the fungi.

The novel compounds may be converted into the usual formulations, e.g. solutions, emulsions, suspensions, dusts, powders, pastes and granules. The forms of application depend entirely on the purpose for which the agents are being used; they should at all events ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt% of active ingredient.

The application rates depend on the effect desired, and range from 0.02 to 3 kg of active ingredient per hectare, or more. The novel compounds may also be used for protecting materials, e.g., for combatting wood-destroying fungi such as *Coniophora puteana* and *Polystictus versicolor*. The novel active ingredients may also be employed as fungicidally effective components of oily wood preservatives for protecting wood against wood-discoloring fungi. The agents are applied by treating, e.g., impregnating or painting, the wood with them.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 13 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 49 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 51 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 70 parts by weight of powdered silica gel, and triturated in a hammer mill. By uniformly distributing the mixture in water, a spray liquor is obtained.

VI. 3 parts by weight of compound no. 62 is intimately mixed with 97 parts by weight of particulate kaolin. A dust is obtained containing 3% by weight of the active ingredient.

VII. 30 parts by weight of compound no. 63 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 4 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 13 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The novel active ingredients may also be mixed and applied with other active ingredients, e.g., herbicides, insecticides, growth regulators, other fungicides and fertilizers. When mixed with other fungicides, the spectrum of fungicidal action is in many cases increased. The following list of fungicides with which the compounds according to the invention may be combined is intended to illustrate, and not restrict, the combination possibilities. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate
and
N,N'-polyethylene-bis-(thiocarbamoyl)-disulfide
ammonia complex of zinc-(N,N'-propylene-bisdithiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothioate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorhlorophenyl)-3-pyridinemethanol
1,2-bis-(3-ethoxycarbonyl-2-thioureido)-benzene
1,2-bis-(3-methoxycarbonyl)-2-thioureido)-benzene
5-butyl-2-dimethylamino-4-hydroxy-6-methylpyrimidine
bis-(p-chlorophenyl)-3-pyridinemethanol
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-(methoximino)-acetamide
1-(2-(2,4-dichlorophenyl)-pentyl)-1H-1,2,4-triazole
2,3-difluoro-alpha-(1H-1,2,4-triazol-1-ylmethyl)-benzhydryl alcohol.

For the following experiments the prior art compounds N-[3-(4-tert-butylphenyl)-2-methylpropyl]-4-hydroxypiperidine (B) and N-[3-(4-tert-butylphenyl)-2-methylpropyl]-3-hydroxymethylpiperidine (A) were used for comparison purposes.

Experiment 1

Action on wheat mildew

Leaves of pot-grown wheat seedlings of the "Frühgold" variety were sprayed with aqueous liquors, the solids of which consisted of 80% (by weight) of active ingredient and 20% of emulsifier, and dusted, 24 hours after the sprayed-on layer had dried, with spores of wheat mildew (*Erysiphe graminis* var. tritici). The plants were then placed in a greenhouse at 20° to 22° C. and 75 to 80% relative humidity. The extent of mildew spread was determined after 7 days.

The results show that compounds 1, 4, 13, 49, 51, 62 and 63, applied as 0.025 and 0.006% spray liquors, had a better fungicidal action (97%) than prior art active ingredient A (90%).

Experiment 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first place for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results show that compounds 8, 13, 49, 51 and 63, applied as 0.05% spray liquors, had a better fungicidal action (97%) than prior art active ingredients A and B (70%).

We claim:

1. A piperidine of the formula where
- $R^1$ is hydrogen, $C_1$–$C_6$-alkyl or halogen,
- $R^2$ and $R^3$ are hydrogen or $C_1$–$C_6$-alkyl,
- $R^4$ is hydrogen, $C_1$–$C_6$-alkyl, allyl, propargyl, trichloroallyl, benzyl, halobenzyl, $C_1$–$C_4$-alkylbenzyl, trifluoromethylbenzyl, alpha-naphthyl methyl or betanaphthyl methyl $COR^5$, $CO_2R^6$ or $CONR^7R^8$,
- $R^5$ and $R^6$ are $C_1$–$C_4$-alkyl, unsubstituted phenyl or halo- or $C_1$–$C_4$-alkyl substituted phenyl or unsubstituted or halo-substituted benzyl
- $R^7$ and $R^8$ are hydrogen, $C_1$–$C_4$-alkyl, phenyl, halophenyl, benzyl or halobenzyl and
- n is 0, 1, 2 or 3, or a plant-tolerated acid addition salt thereof, with the proviso that, when $R^4$ is hydrogen, acetyl or propionyl, n is not 0 or 1 and $R^1$, $R^2$ and $R^3$ are not hydrogen, and with the further proviso that when n is 2, $R^4$ is not hydrogen, and with the further proviso that when n is 0, $R^2$ is not hydrogen or methyl.

2. A fungicidal composition containing a solid or liquid carrier and a fungicidally effective amount of a piperidine of the formula where
- $R^1$ is hydrogen, $C_1$–$C_6$-alkyl or halogen,
- $R^2$ and $R^3$ are hydrogen or $C_1$–$C_6$-alkyl,
- $R^4$ is hydrogen, $C_1$–$C_6$-alkyl, allyl, propargyl, trichloroallyl, benzyl, halobenzyl, $C_1$–$C_4$-alkylbenzyl, trifluoromethylbenzyl, alpha-naphthyl methyl or betanaphthyl methyl $COR^5$, $CO_2R^6$ or $CONR^7R^8$,
- $R^5$ and $R^6$ are $C_1$–$C_4$-alkyl, unsubstituted phenyl or halo- or $C_1$–$C_4$-alkyl substituted phenyl or unsubstituted or halo-substituted benzyl
- $R^7$ and $R^8$ are hydrogen, $C_1$–$C_4$-alkyl, phenyl, halophenyl, benzyl or halobenzyl and
- n is 0, 1, 2 or 3, or a plant-tolerated acid addition salt thereof, with the proviso that, when $R^4$ is hydrogen, acetyl or propionyl, n is not 0 or 1 and $R^1$, $R^2$ and $R^3$ are not hydrogen, and with the further proviso that when n is 2, $R^4$ is not hydrogen, and with the further proviso that when n is 0, $R^2$ is not hydrogen or methyl.

3. A process for combatting fungi, wherein a fungicidally effective amount of a piperidine of the formula where
- $R^1$ is hydrogen, $C_1$–$C_6$-alkyl or halogen,
- $R^2$ and $R^3$ are hydrogen or $C_1$–$C_6$-alkyl,
- $R^4$ is hydrogen, $C_1$–$C_6$-alkyl, allyl, propargyl, trichloroallyl, benzyl, halobenzyl, $C_1$–$C_4$-alkylbenzyl, trifluoromethylbenzyl, alpha-naphthyl methyl or betanaphthyl methyl $COR^5$, $CO_2R^6$ or $CONR^7R^8$,
- $R^5$ and $R^6$ are $C_1$–$C_4$-alkyl, unsubstituted phenyl or halo- or $C_1$–$C_4$-alkyl substituted phenyl or unsubstituted or halo-substituted benzyl
- $R^7$ and $R^8$ are hydrogen, $C_1$–$C_4$-alkyl, phenyl, halophenyl, benzyl or halobenzyl and
- n is 0, 1, 2 or 3, or a plant-tolerated acid addition salt thereof, with the proviso that, when $R^4$ is hydrogen, acetyl or propionyl, n is not 0 or 1 and $R^1$, $R^2$ and $R^3$ are not hydrogen, and with the further proviso that when n is 2, $R^4$ is not hydrogen, and with the further proviso that when n is 0, $R^2$ is not hydrogen or methyl is allowed to act on materials, areas, plants or seed threatened by fungi or fungal attack.

* * * * *